US005753610A

United States Patent [19]

Harada et al.

[11] Patent Number: 5,753,610

[45] Date of Patent: May 19, 1998

[54] PERFUME CONTAINING (6E) -2,3-DIHYDROFARNESOL

[75] Inventors: Makoto Harada; Hiroyuki Matsuda; Takeshi Yamamoto, all of Kanagawa, Japan

[73] Assignee: Takasago International Corporation, Tokyo, Japan

[21] Appl. No.: 609,903

[22] Filed: Feb. 29, 1996

[30] Foreign Application Priority Data

Mar. 8, 1995 [JP] Japan .................................... 7-074679

[51] Int. Cl.[6] ................................ A61K 7/46; C11B 9/00

[52] U.S. Cl. .................................................. 512/25; 512/5

[58] Field of Search .............................. 514/739; 512/25, 512/5

[56] References Cited

U.S. PATENT DOCUMENTS

| | | | |
|---|---|---|---|
| 4,220,665 | 9/1980 | Klein | 424/343 |
| 4,481,217 | 11/1984 | Yamatsu et al. | 424/311 |
| 4,962,242 | 10/1990 | Yamada et al. | 568/822 |

OTHER PUBLICATIONS

Narendra Kumar et al, *Phytochemistry*, vol. 25, pp. 250–253, 1986, "Volatile Constituents of of Peony Flowers".

Zhongguo Zhongyao Zazhi, vol. 15, No. 11, pp. 680–682 (1990).

Nippon Suisangakkai-shi, vol. 56, No. 6, pp. 973–983 (1990).

Zhiwu Xuebao, vol. 31, No. 4, pp.289–295 (1989).

Spipin Kexue (Beijing), vol. 91, pp. 45–47 (1987).

Pollena; Tluszcze, Srodki Piorace, Kosmet, vol. 30, pp. 143–145 (1990).

J. Nat. Prod., vol. 49, pp. 1169–1171 (1986).

Zoon, Suppl., No. Suppl. 1, pp. 61–65 (1973).

Insects Soc., vol. 24, No. 2, pp. 213–224 (1977).

J. Chem. Ecol., vol. 17, pp. 1633–1639 (*1991).

Izv. Akad. Nauk SSSR. Ser Khim, No. 3, pp. 699–700 (1989).

Acta Chem. Scand., vol. 25, No. 5, pp. 1685–1694 (1971).

Indian J. Chem. Sect. B, vol. 188, No. 1, pp. 31–32 (1979).

*Primary Examiner*—Raymond J. Henley, III

*Attorney, Agent, or Firm*—Sughrue, Mion, Zinn, Macpeak & Seas, PLLC

[57] ABSTRACT

A perfume containing (6E)-2,3-dihydrofarnesol represented by the following general formula (I):

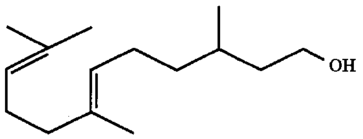

(I)

which has a purity of the trans form of more than 50% by weight, is disclosed. A muguet perfume containing the above compound is excellent in fragrance qualities and having a high safety without any sensitization and an antimicrobial activity.

2 Claims, No Drawings

PERFUME CONTAINING (6E) -2,3-DIHYDROFARNESOL

FIELD OF THE INVENTION

This invention relates to a perfume containing (6E)-2,3-dihydrofarnesol, which has a purity of the trans form of more than 50% by weight, to be used in perfuming toiletries a perfume containing the (3S)-form of the (6E)-2,3-dihydrofarnesol.

BACKGROUND OF THE INVENTION

It has been known that 2,3-dihydrofarnesol occurs in animals and plants in nature. Regarding plants, for example, there has been reported that 2,3-dihydrofarnesol is contained in the essential oil of *Lonicera japonica* Thunb [ZHONGGUO ZHONGYAO ZAZHI, Vol. 15, No. 11, pp. 680–682 (1990)], Marine brouno and Red algae [Nippon Suisangakkai-shi, Vol. 56, No. 6, pp. 973–983 (1990)], the essential oil of Ku-Shi Rose [Zhiwu Xuebao., Vol. 31, No. 4, pp. 289–295 (1989)], the peel of *Pyrus bretschneideri* [Spipin Kexue (Beijing), Vol. 91, pp. 45–47 (1987)], Peony flower [Pollena; Tluszcze, Srodki Piorace, Kosmet. Vol. 30, pp. 143–145 (1986) and Phytochemistry, Vol. 25, pp. 250–253 (1986)] and *Fagara macrophylla* and *Zanthoxylum rigidifolium* pericarps [J. Nat. Prod., Vol. 49, pp. 1169–1171 (1986)]. It has been also known that 2,3-dihydrofarnesol is contained in the secretes of insects such as *Bombus jonellus* males [Zoon, Suppl., No. Suppl. 1, pp. 61–65 (1973)], North European Phyrobombus [Insects Soc., Vol. 24, No. 2, pp. 213–224 (1977)] and Workers of an army ant [J. Chem. Ecol., Vol. 17, pp. 1633–1639 (1991)].

In addition, 2,3-dihydrofarnesol is cited as one of the volatile components of *Paeoniae Radix* [Phytochemistry, Vol. 25, No. 1, pp. 250–253 (1986)]. However there has been reported neither the particular fragrance, the fragrance strength, the sensitization nor the antimicrobial activity of 2,3-dihydrofarnesol. Furthermore, none of these reports states the geometrical isomers of this compound.

Examples of the synthesis of the optically active isomers of 2,3-dihydrofarnesol are reported in Izv. Akad. Nauk SSSR. Ser Khim, No. 3, pp. 699–700 (1989), JP-A-63-152337 (the term "JP-A" as used herein means an "unexamined published Japanese patent application"), Acta Chem. Scand., Vol. 25, No. 5, pp. 1685–1694 (1971) and Indian J. Chem. Sect. B, Vol. 188, No. 1, pp. 31–32 (1979). However, there has never been reported the fragrance of the optically active isomers of 2,3-dihydrofarnesol. As a matter of course, it has never been reported that this compound is employed as a perfume.

In recent years, public interest in safety has been increasing and thus there is a growing tendency toward stricter standards of mutagenicity, accumulation, biodegradability, temporary skin irritation, skin sensitization, phototoxicity and safety of perfumes. Although typical examples of muguet-like floral perfumes (α-methyl-p-t-butylphenylpropionaldehyde, cyclamen aldehyde, etc.) are excellent in fragrance, the use of these perfumes on a mass scale is restricted due to the skin sensitization thereof. It is therefore required to develop safe muguet perfumes free from sensitization.

In recent years, there has been required a multifunctional perfume, i.e., a perfume having added values. In particular, it has been desired to develop a perfume having an antimicrobial activity to be used in cosmetics.

Accordingly, an object of the present invention is to provide a muguet perfume which has not only excellent fragrance qualities but also other functions, for example, a high safety without any sensitization and an antimicrobial activity.

Under these circumstances, the present inventors have conducted extensive studies. As a result, they have successfully found out that (6E)-2,3-dihydrofarnesol represented by the following general formula (I):

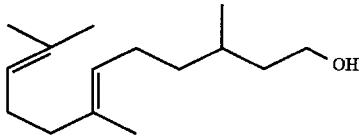

(I)

which has a purity of the trans form of more than 50% by weight, has an intense cyclamen-like floral fragrance falling within the category of the muguet-like fragrance and, at the same time, a high safety without any sensitization and an antimicrobial activity, thus completing the present invention.

The present inventors have further studied the optically active isomers of (6E)-2,3-dihydrofarnesol and consequently found out that the (3S)-form of (6E)-2,3-dihydrofarnesol has a clean, graceful and long-lasting fragrance similar to cyclamen, while the (3R)-form thereof has only a weak fragrance with a somewhat metallic and balsamic side note. That is to say, the (3S)-form is excellent in fragrance while the (3R)-form has a poor value in fragrance.

SUMMARY OF THE INVENTION

The present invention relates to a perfume containing (6E)-2,3-dihydrofarnesol represented by the following general formula (I):

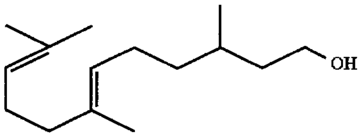

(I)

which has a purity of the trans form of more than 50% by weight.

The present invention further relates to a perfume containing (3S)-(6E)-2,3-dihydrofarnesol, which is the (3S)-form of the above-mentioned (6E)-2,3-dihydrofarnesol, represented by the following general formula (II):

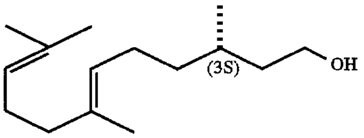

(II)

DETAILED DESCRIPTION OF THE INVENTION

The (6E)-2,3-dihydrofarnesol of the present invention can be easily synthesized by selectively hydrogenating farnesol in the presence of a catalyst. As the catalyst, use can be made of Ru-carbon, Rh-carbon, Ru-alumina, amines such as pyridine, and nickel or palladium poisoned with a sulfur compound such as carbon disulfide.

Optically active (3S)-(6E)-2,3-dihydrofarnesol can be synthesized by asymmetrically hydrogenating farnesol in the presence of an optically active ruthenium-BINAP catalyst [for example, $Ru_2Cl_4((R)\text{-}T\text{-}BINAP)_2NEt_3$, wherein (R)-T-BINAP represents (R)-2,2'-bis[di(p-tolyl)phosphino]-1,1'-binaphthyl, and Et represents ethyl] (JP-A-63-152337).

The trans-rich compound thus obtained, i.e., (6E)-2,3-dihydrofarnesol having a purity of the trans form of more than 50% by weight has very excellent fragrance qualities. More particularly, when the content of the trans form exceeds 50% by weight, a very excellent and intense floral fragrance similar to cyclamen can be obtained. On the other hand, a cis-rich compound, i.e., (6Z)-2,3-dihydrofarnesol containing more than 50% by weight of the cis form shows a not floral but woody fragrance. It has been clarified that the woody fragrance of the cis form affects the floral fragrance of the trans form.

As described above, in the present invention, it is necessary that the content of the trans form is more than 50% by weight, preferably more than 60% by weight, still preferably more than 75% by weight and still more preferably more than 90% by weight. Needless to say, a higher purity is the more desirable.

It has been also found out that the above-mentioned (6E)-2,3-dihydrofarnesol having a purity of the trans form of more than 50% by weight causes no sensitization on the skin. Accordingly, the (6E)-2,3-dihydrofarnesol can be used safely without any fear of sensitization, different from α-methyl-p-t-butylphenylpropionaldehyde, cyclamen aldehyde, etc. That is to say, farnesol, which is an analog of 2,3-dihydrofarnesol, causes sensitization on Guinea pig skin at a concentration of 5% by weight in a sensitization test, while (6E)-2,3-dihydrofarnesol of the present invention causes no sensitization at the same concentration. In a test with the use of human skin, the (6E)-2,3-dihydrofarnesol of the present invention shows no sensitization even at a concentration of 10% (in a lanolin solution), which suggests that it has a high safety.

It has been furthermore found out that the (6E)-2,3-dihydrofarnesol of the present invention has an antimicrobial activity on various bacteria such as *Pseudomonas aeruginosa, Staphylococcus aureus* and indigenous skin bacteria. Regarding the antimicrobial activity, it has been known that farnesol, which is an analog of the compound of the present invention, has an antimicrobial activity (JP-A-60-64913). However, (6E)-2,3-dihydrofarnesol is superior to farnesol in the antimicrobial activity on some bacteria. By using the (6E)-2,3-dihydrofarnesol of the present invention in a perfume, therefore, it is possible to impart not only an excellent fragrance qualities but also an antimicrobial activity.

As discussed above, by using (6E)-2,3-dihydrofarnesol, it is possible to provide a perfume, which has excellent fragrance qualities, a high safety without any sensitization and an antimicrobial activity.

The present inventors have further synthesized optically active isomers of the above-mentioned (6E)-2,3-dihydrofarnesol and examined the fragrance qualities of each isomer. As a result, they have found out that the (3S)-form has a clean, graceful and long-lasting fragrance similar to cyclamen, while the (3R)-form has only a weak fragrance with a somewhat metallic and balsamic side note. That is to say, the (3R)-form has a poor value in fragrance.

It has been also confirmed that (3S)-(6E)-2,3-dihydrofarnesol, i.e., the (3S)-form, has a high safety without any sensitization and an antimicrobial activity similar to the above-mentioned (6E)-2,3-dihydrofarnesol.

Accordingly, by using the (6E)-2,3-dihydrofarnesol of the (3S)-form, which is particularly excellent in the fragrance qualities, it is possible to obtain a very excellent perfume having a fragrance improved in cleanness, elegance and richness.

The (6E)-2,3-dihydrofarnesol or the (3S)-(6E)-2,3-dihydrofarnesol of the present invention may be used in an arbitrary amount without restriction. By taking the balance of the fragrance qualities into consideration, it is recommended to use such a compound in an amount of from 0.01 to 90% by weight, preferably from 1 to 50% by weight, in a perfume.

By using the (6E)-2,3-dihydrofarnesol and the (3S)-(6E)-2,3-dihydrofarnesol of the present invention, therefore, it is possible to provide a perfuming agent or a perfume-improving aid having highly excellent added values which has an excellent fragrance, a high safety without any sensitization and an antimicrobial activity. It is also possible to provide toiletries, sanitary goods, drugs, etc. containing such a compound as a perfume component.

Namely, the compounds of the present invention may be added in an appropriate amount to shampoos, rinses, scents, colognes, hair tonics, hair creams, pomades, bases for hair care products, face powders, lip sticks, bases for cosmetics, cosmetic cleansers, soaps, dish washing detergents, kitchen cleansers, detergents for laundry, softners, disinfection detergents, deodorizing detergents, sanitary detergents, interior aromatics, furniture cares, disinfectants, insecticides, bleaching agents, toothpastes, mouth washers, toilet papers and perfuming agents for facilitating the administration of drugs, etc., thus imparting the unique fragrance and improving the commercial value.

To further illustrate the present invention in greater detail, the following Synthesis Examples, Examples, Test Examples and Formulation Example will be given.

Analytical instruments:

Gas Chromatography 5890 (manufactured by Hewlett-Packard, Ltd.)

column: PEG CBP-20 (0.25 mm×25 m)

temperature: elevating from 100° C. to 220° C. at a rate of 10° C./min.

angle of rotation: polarimeter DIP-4 (manufactured by Nippon Bunko Kogaku K.K.).

Synthesis Example 1

Synthesis of (6E)-2,3-dihydrofarnesol 6.66 g (30 mmol) of farnesol [(2E,6E)-form : (2E,6Z)-form: (2Z,6E)-form: (2Z,6Z)-form=1:1:1:1] and 0.3 g of Ru-carbon (carriage: 5%) were introduced into a 100 ml autoclave under a nitrogen atmosphere and sufficiently purged with nitrogen. Then 33 ml of methanol was added thereto under a nitrogen atmosphere. After the replacement with hydrogen, the hydrogen pressure was regulated to 40 atm and the reaction mixture was stirred at 120° C. for 16 hours. After the completion of the reaction, a portion of the reaction mixture was taken up and the conversion ratio was measured by gas chromatography. Thus it was found out that the conversion ratio was 100%.

The reaction mixture was concentrated under reduced pressure to thereby give 5.2 g of a fraction. When the composition was analyzed by gas chromatography, it comprised 52% of the (6E)-form and 48% of the (6Z)-form.

A 3 g portion of this fraction was treated with silica gel column chromatography carrying 3 g of silver nitrate. Thus 0.6 g of a fraction rich in the cis form [(6Z)-form 85%, (6E)-form 15%] was obtained.

Synthesis Example 2

Synthesis of (6E)-2,3-dihydrofarnesol 6.66 g (30 mmol) of trans-farnesol [(2E,6E)-form/(2Z,6E)-form=99/1] and 0.3 g of Ru-carbon (carriage: 5%) were introduced into a 100 ml autoclave under a nitrogen atmosphere and sufficiently purged with nitrogen. Then 33 ml of methanol was added thereto under a nitrogen atmosphere. After the replacement with hydrogen, the hydrogen pressure was regulated to 40 atm and the reaction mixture was stirred at 120° C. for 16 hours. After the completion of the reaction, a portion of the reaction mixture was taken up and the conversion ratio was measured by gas chromatography. Thus it was found out that the conversion ratio was 100%. The reaction mixture was concentrated under reduced pressure to thereby give a fraction. When the composition was analyzed by gas chromatography, it comprised more than 99% of the (6E)-form.

Synthesis Example 3

Synthesis of (3S)-(6E)-2,3-dihydrofarnesol 6.66 g (30 mmol) of trans-farnesol [(2E,6E)-form/(2Z,6E)-form=99/1] and 90 mg (0.1 mmol) of $Ru_2Cl_4((R)\text{-T-BINAP})_2NEt_3$[(R)-T-BINAP being (R)-2,2'-bis[di(p-tolyl)phosphino]-1,1'-binaphthyl, and Et being ethyl] were introduced into a 100 ml autoclave under a nitrogen atmosphere and sufficiently purged with nitrogen. Then 33 ml of methanol was added thereto under a nitrogen atmosphere. After the replacement with hydrogen, the hydrogen pressure was regulated to 40 atm and the reaction mixture was stirred at room temperature for 16 hours. After the completion of the reaction, a portion of the reaction mixture was taken up and the conversion ratio was measured by gas chromatography. Thus it was found out that the conversion ratio was 100%. The reaction mixture was concentrated under reduced pressure. Then the crude product thus obtained was distilled under reduced pressure to thereby give 5.45 g (yield: 82%) of the title compound having a purity of 96%.

The angle of rotation of this product was −3.92° ($[\alpha]_D^2$ −3.92° (C=20, chloroform)).

Thus it was proved that the optical purity thereof was 89% ee (calculated from the data reported in Acta. Chem. Scand., 1971, Vol. 25, pp. 1685–1694).

Regarding the cis/trans isomerism, the trans form (6-position) of the starting material was maintained as such. Thus the ratio of the (6E)-form was 100%.

Synthesis Example 4

Synthesis of (3R)-(6E)-2,3-dihydrofarnesol

The same reaction as the one of the above Synthesis Example 3 was performed but replacing $Ru_2Cl_4((R)\text{-T-BINAP})_2NEt_3$ by $Ru_2Cl_4((S)\text{-T-BINAP})_2NEt_3$. Thus 5.65 g (yield: 84%) of the title compound having a purity of 95% (measured by gas chromatography) was obtained. The angle of rotation of this product was +3.97° ($[\alpha]_D^{24}$ +3.97° (C=20, chloroform)). Thus it was proved that the optical purity thereof was 90% ee.

EXAMPLE 1

Evaluation of fragrance qualities

Seven skilled panelists examined differences in the fragrance qualities of (a) the (6E)-2,3-dihydrofarnesol of a purity of 99% or above synthesized in Synthesis Example 2, (b) the (6E)-2,3-dihydrofarnesol of a purity of 52% synthesized in Synthesis Example 1, and (c) the 2,3-dihydrofarnesol consisting of 15% of the trans form and 85% of the cis form synthesized in Synthesis Example 1. As a result, the fragrance of (a) was the strongest and sharp, clean, graceful and floral similar to cyclamen, while (c) containing less than 50% of the trans form showed a metallic, woody and green fragrance with a poor floral feel. That is to say, the compounds (a) and (c) largely differed from each other in fragrance qualities, i.e., showed completely different fragrances.

The compound (a) was highly useful as a cyclamen-like floral perfume, while the compound (c) was poor in the perfume value due to its metallic and woody fragrance. The compound (b), which contained 52% of the trans-form, was usable as a cyclamen-like floral perfume, though it was somewhat inferior to the compound (a) in the floral feel, fragrance intensity and richness.

EXAMPLE 2

Evaluation of fragrance qualities

Seven skilled panelists examined differences in the fragrance qualities of (a) the (6E)-2,3-dihydrofarnesol synthesized in Synthesis Example 2, (d) the (3S)-(6E)-2,3-dihydrofarnesol synthesized in Synthesis Example 3, and (e) the (3R)-(6E)-2,3-dihydrofarnesol synthesized in Synthesis Example 4. As a result, the fragrance of the compound (d) was somewhat stronger than that of the compound (a) and long-lasting, clean, graceful and floral similar to cyclamen. In contrast, the compound (e) showed a weak fragrance with a not floral but somewhat metallic and balsamic side note. Thus the compound (e) had a fragrance different from that of the compound (d) and was poor in the perfume value.

Test Example 1

Skin sensitization test

A sensitization test with the use of Guinea pigs was carried out in accordance with the Magnusson method by using (a) the (6E)-2,3-dihydrofarnesol of a purity of 99% or above, (b) the (6E)-2,3-dihydrofarnesol of a purity of 52% and (d) the (3S)-(6E)-2,3-dihydrofarnesol. As a result, none of the test compounds caused sensitization at a concentration of 5%.

Then the same test was performed by using farnesol [(2E,6E)-form: (2E,6Z)-form: (2Z,6E)-form: (2Z,6Z)-form= 1:1:1:1] which was an analog of the (6E)-2,3-dihydrofarnesol of the present invention. As a result, it caused sensitization at a concentration of 5%.

Test Example 2

Patch test

The above-mentioned compounds (a), (b) and (d) were each dissolved in lanolin to give a concentration of 10%. The obtained solution was then applied onto patches (Finnchamber, manufactured by Taisho Pharmaceutical Co., Ltd.). These patches were adhered to the inside of upper arms of 30 subjects. After 24 hours, the patches were peeled from the skin and the skin irritation was examined. Further, the skin irritation was examined after the subsequent 24 hours. As a control, patches to which lanolin alone had been applied were employed. As a result, all of the 30 subjects suffered from no skin irritation within the first 24 hours and the subsequent 24 hours. Thus it has been proved that the compounds (a), (b) and (d) of the present invention are highly safe to human skin too.

Test Example 3

Antibacterial test

The minimum inhibitory concentrations of (6E)-2,3-dihydrofarnesol synthesized in Synthesis Example 1 on bacteria listed in Table 1 were determined in the following manner by the step dilution method in an agar medium.

10 g of brain heart infusion medium (manufactured by Nissui Seiyaku K.K.), 10 g of dry bouillon (manufactured by Nissui Seiyaku K.K.), 4 g of yeast extract powder (manufactured by Difco Laboratories) and 14 g of agar were added to 1,000 ml of distilled water and dissolved therein by heating. Then the obtained solution was pipetted in 10 ml portions into test tubes and sterilized under elevated pressure. Then it was heated again and sustained in the state of a solution. Subsequently, each test solution and ethanol or DMSO (dimethyl sulfoxide) free from any antimicrobial compound of the present invention (employed as a control) were added thereto in amounts of 5 to 200 µl. After mixing, the solutions were poured into plastic Petri dishes (inner diameter: 90 mm) and solidified.

The medium thus solidified in each Petri dish was divided into 9 parts. Then 5 µl portions of suspensions of the test microorganisms except acne bacteria in distilled water (cell or spore count: $10^8$–$10^9$/ml) were inoculated thereinto and incubated at 30° C. for 48 hours. Then the growth of each microorganism was observed with the naked eye to thereby determine the minimum inhibitory concentration (MIC).

In the case of the acne bacteria, a GAM medium (manufactured by Nissui Seiyaku K.K.) was pipetted in 6 ml portions into screwed test tubes (10×105 mm) and sterilized. After adding sample solutions, a culture medium of the acne bacteria was inoculated in 5 µl portions and incubated at 37° C. for 48 hours followed by the judgement of the growth.

As the results given in Table 1 show, an antimicrobial activity was observed even at a concentration of 30 ppm or less. In particular, the minimum inhibitory concentrations on *Pseudomonas aeruginosa* and *Bacillus subtilis* were 20 ppm. Also, an antimicrobial activity was exerted on the acne bacteria even at a concentration of 10 ppm or less. Thus it has been proved that the compounds of the present invention are highly excellent in antimicrobial activity.

Further, the (6E)-2,3-dihydrofarnesol synthesized in Synthesis Example 2 and the (3S)-(6E)-2,3-dihydrofarnesol synthesized in Synthesis Example 3 were subjected to the same test by using the bacteria listed in Table 1. The results thus obtained were almost the same as those described above, though some differences were observed.

TABLE 1

| Concentration (ppm) | *Pseudomonas aeruginosa* | *Staphylococcus aureus* | Skin indigenoua bacteria | *Bacillus subtilis* | Acne bacteria | Coryne bacteria |
|---|---|---|---|---|---|---|
| 100 | – | – | – | – | – | – |
| 50 | – | – | – | – | – | – |
| 30 | – | – | – | – | – | – |
| 20 | – | + | + | – | – | – |
| 10 | + | + | + | + | – | + |

When commercially available farnesol [(2E,6E)-form (2E,6Z)-form: (2Z,6E)-form: (2Z,6Z)-form=1:1:1:1], which was an analog of the (6E)-2,3-dihydrofarnesol of the present invention and known as an antimicrobial compound, was subjected to the same test with the use of *Staphylococcus aureus*, indigenous skin bacteria and coryne bacteria, the minimum inhibitory concentrations were respectively 50, 50 and 25 ppm. Thus it can be understood that the compounds of the present invention are superior in antimicrobial activity to farnesol, which has been known as an antimicrobial agent, and thus usable as an antimicrobial agent too.

Formulation Example 1

By using the (6E)-2,3-dihydrofarnesol synthesized in Synthesis Example 2, a muguet base having a high preference of the following composition was prepared.

Muguet base

| Component | part by weight |
|---|---|
| L-citronellol | 120 |
| L-hydroxycitronellal | 100 |
| Kovanol (manufactured by Takasago International Corporation) [4-(4-hydroxy-4-methylpentyl)-3-cyclohexen-1-carboxyaldehyde | 80 |
| Lilial (manufactured by Givaudan) (α-methyl-p-t-butylphenylpropionaldehyde) | 100 |
| Suzaral (manufactured by Takasago International Corporation) (α-methyl-p-isobutylphenyl-propionaldehyde) | 30 |
| benzyl acetate | 100 |
| linalool | 100 |
| hexylcinnamic aldehyde | 100 |
| terpineol | 40 |
| styrax | 40 |
| indole 5% benzyl acetate solution | 10 |
| (6E)-2,3-dihydrofarnesol synthesized in Synthesis Example 2 | 180 |
| total | 1,000 |

A perfume of the present invention, which contains (6E)-2,3-dihydrofarnesol having a purity of the trans form of more than 50% by weight or the (3S)-form thereof, has a strong and floral fragrance similar to cyclamen. Further, it is a highly safe compound and can be used without any fear of sensitization. Furthermore, it is an excellent perfume having an added value of an antimicrobial activity.

While the invention has been described in detail and with reference to specific embodiments thereof, it will be apparent to one skilled in the art that various changes and modifications can be made therein without departing from the spirit and scope thereof.

What is claimed is:

1. A perfume containing (6E)-2,3-dihydrofarnesol represented by the following general formula (I):

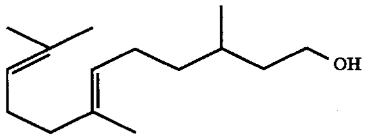

(I)

which has a purity of the trans form of more than 50% by weight, wherein said (6E)-2,3-dihydrofarnesol is (3-racemic)-(6E)-2,3-dihydrofarnesol.

2. A method of imparting a fragrance to a host which comprises applying to said host a perfume containing (6E)-2,3-dihydrofarnesol represented by the following general formula (I):

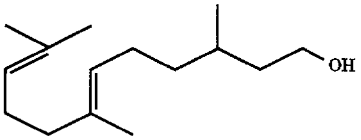
(I)
which has a purity of the trans form of more than 50% by weight, wherein said (6E)-2,3-dihydrofarnesol is selected from the group consisting of (3S)-(6E)-2,3-dihydrofarnesol and (3-racemic)-(6E)-2,3-dihydrofarnesol.
* * * * *